United States Patent [19]

Kimura et al.

[11] Patent Number: 4,476,109
[45] Date of Patent: Oct. 9, 1984

[54] METHOD OF PREPARING GAMMA GLOBULIN SUITABLE FOR INTRAVENOUS ADMINISTRATION

[75] Inventors: Tokusuke Kimura, Tokyo; Fumio Kurosu, Hasuda; Toshitsugu Inouchi, Koganei; Masana Komatsu, Tanashi, all of Japan

[73] Assignee: Fujirebio Kabushiki Kaisha, Tokyo, Japan

[21] Appl. No.: 423,418

[22] Filed: Sep. 24, 1982

[30] Foreign Application Priority Data

Sep. 29, 1981 [JP] Japan .................................. 56-153133

[51] Int. Cl.³ ..................... A61K 39/00; A61K 45/02; A23J 00/00; C07G 7/00
[52] U.S. Cl. ................................ 424/85; 260/112 R; 260/112 B
[58] Field of Search .......................... 424/85, 86, 177; 260/112 R, 112 B

[56] References Cited

U.S. PATENT DOCUMENTS

| | | | |
|---|---|---|---|
| 2,793,203 | 5/1957 | Schultze et al. | 424/87 |
| 4,021,540 | 5/1977 | Pollack | 424/86 |
| 4,165,370 | 8/1979 | Coval | 424/85 |
| 4,168,303 | 9/1979 | Nishida et al. | 424/85 |
| 4,276,283 | 6/1981 | Eibl et al. | 424/85 |
| 4,296,027 | 10/1981 | Condie | 260/112 B |
| 4,374,763 | 2/1983 | Tokagi | 260/112 B |

OTHER PUBLICATIONS

Oncley, "The Separation of the Antibodies, Isoagglutinins, Prothrombin, Plasminogen and $\beta_1$-Lipoprotein into Subfractions of Human Plasma", Feb., 1949, vol. 71, pp. 541-550.

Cohn, "Preparation and Properties of Serum and Plasma Proteins. IV. A System for the Separation into Fractions of the Protein and Lipoprotein Components of Biological Tissues and Fluids", Mar. 1946, vol. 68, pp. 459-475.

*Primary Examiner*—Lionel M. Shapiro
*Assistant Examiner*—Robin Lyn Teskin
*Attorney, Agent, or Firm*—Flynn, Thiel, Boutell & Tanis

[57] ABSTRACT

A method of preparing gamma globulin suitable for intravenous administration comprising a first step of treating a supernatant liquid separated from human blood plasma with ethanol under conditions of a pH of 5.5 to 6.5, an ethanol concentration of 30 to 35%, and a protein concentration of 1 to 2% by weight.

3 Claims, No Drawings

METHOD OF PREPARING GAMMA GLOBULIN SUITABLE FOR INTRAVENOUS ADMINISTRATION

The present invention relates to a method of preparing a gamma ($\gamma$) globulin composition suitable for intravenous administration. More particularly, the present invention relates to a method of preparing a gamma ($\gamma$) globulin composition containing albumin and not containing aggregates of gamma globulin.

BACKGROUND OF THE INVENTION

Gamma globulin is widely used as a therapeutic agent, and generally, it is administered by intramuscular injection. Impurities, such as aggregates of gamma globulin occasionally contained in gamma globulin products, render hazardous the administration of such gamma globulin products by intravenous injection.

Accordingly, for the purpose of preparing gamma globulin compositions free of aggregates thereof, there have been proposed methods of preparing gamma globulin under such conditions that aggregates are not produced. There have also been proposed methods of removing any aggregates that are produced in the course of preparing the gamma globulin, which removal takes place at the last step of the procedure. Such methods for the production or purification of gamma globulin have been disclosed in the literature, for instance, U.S. Pat. Nos. 3,415,804, 3,763,135 and 4,093,606, and British Pat. No. 1,372,953.

It is an object of this invention to provide a method of preparing gamma globulin, not containing aggregates of gamma globulin, under conditions different from those disclosed in the patents mentioned above.

The inventors have found that gamma globulin products containing albumin in certain quantities can be obtained by treating a supernatant liquid, separated from human blood plasma, with ethanol, under selected conditions as described in the following. In the invention process, the production of gamma globulin aggregates can be prevented, and gamma globulin products suitable for intravenous administration can be obtained in a high yield, which products contain a certain small quantity of albumin and do not contain gamma globulin aggregates. The present invention is based on this discovery.

SUMMARY OF THE INVENTION

The method of separating gamma globulin from human blood plasma by fractional precipitation with ethanol is known as the Cohn procedure, described in J. Amer. Chem. Soc., 68, 459-75 (1946). The method of the present invention is an improvement of the so-called Cohn Method 9, as described in J. Amer. Chem. Soc. 71, 541-50 (1949). In the Cohn Method 9, a supernatant liquid containing albumin and a precipitate consisting of gamma globulin can be obtained by treating human blood plasma with ethanol, under conditions of pH 6.9, an ethanol concentration 25 vol. %, and a protein concentration 3.0 wt. %.

In contrast, in the method of the present invention, a first supernatant liquid is obtained by adding ethanol to human blood plasma under conditions effective to precipitate a first precipitate containing most of the fibrinogen that was contained in the starting blood plasma, while minimizing the amounts of albumin and gamma globulin contained in the first precipitate, and then separating the first supernatant liquid from the first precipitate. Suitable conditions for this first precipitation are an ethanol concentration of 8 to 9 vol. % and a temperature of from 0° to −3° C. A second supernatant liquid containing albumin and a second precipitate consisting of gamma globulin and albumin, preferably containing from 15 to 20 wt. % albumin, is then obtained by adding ethanol and a buffer to the first supernatant liquid to provide the conditions of pH 5.5 to 6.5, an ethanol concentration 30 to 35 vol. %, and a protein concentration of 1.0 to 2.0 wt. %. The mixture is allowed to stand at about −5° C. until the second precipitate is formed. Then the mixture is centrifuged to separate the supernatant liquid from the second precipitate (PI). The protein concentration in this second precipitation step is the total concentration of albumin, globulins, and other proteins contained in the first supernatant liquid. The ionic strength of the mixture in the second precipitation step is about 0.08. The ionic strength is the ionic strength of electrolytes in the first supernatant liquid, and is equal to $\frac{1}{2}\Sigma MI \times (ZI)^2$, wherein MI is molar concentration of ions and ZI is the valence thereof. The second precipitate (PI) consisting of gamma globulin and albumin is precipitated out under these conditions.

In this process, the separation steps are typically carried out by centrifugation.

A gamma globulin composition suitable for intravenous administration, that is, a composition not containing aggregates of gamma globulin, can then be obtained by a further step of purifying the second precipitate (PI) consisting of gamma globulin and albumin obtained as described above by one of the following methods (1) or (2). The purified gamma globulin suitable for intravenous administration, obtained by methods (1) and (2), typically consists of 90 to 95 wt. % of gamma globulin and 5 to 10 wt. % of albumin.

Method (1). The second precipitate (PI), obtained as described above, is suspended in distilled water, and the pH of the suspension is adjusted to a value in the range of 4.0 to 5.0 by adding a buffer. Ethanol is added to this suspension to provide an ethanol concentration of 10 to 16 vol. %. The mixture is allowed to stand at −5° C. until the third precipitate is formed. The mixture is then centrifuged to separate the third precipitate from the third supernatant liquid. The resulting third supernatant liquid is then freeze-dried to form the gamma globulin product.

Instead of directly freeze-drying the third supernatant liquid, this third supernatant liquid can instead be adjusted to pH 4.0 to 5.0, and then further ethanol is added thereto to provide an ethanol concentration of 20 to 25 vol. %. This mixture is allowed to stand at −5° C. until a fourth precipitate is formed and then the mixture is centrifuged to separate the fourth precipitate, which is discarded, whereby to obtain a fourth supernatant liquid. The resulting fourth supernatant liquid is freeze-dried to form the gamma globulin product.

Method (2). The precipitate (PI), obtained as described above, is suspended in distilled water, and the pH of the suspension is adjusted to a value in the range of 4.5 to 5.0 by adding a buffer. Ethanol is added to this suspension to provide an ethanol concentration of 20 to 25 vol. %. The mixture is allowed to stand at −5° C. until a third precipitate is formed and then is centrifuged to separate the third precipitate from the third supernatant liquid. The third supernatant liquid is adjusted to a pH of 4.5 to 5.0 and is adjusted to an ethanol concentration 20 to 25 vol. % by addition of ethanol, and to an ionic strength of about 0.1 by addition of NaCl. The mixture is allowed to stand until a fourth precipitate is formed and then the resulting fourth precipitate is separated by centrifugation and then is dried to form the gamma globulin product.

EXAMPLES

Three examples of the present invention are described below. The examples are for illustrative purposes only and do not limit the scope of the invention. Ethanol concentrations are volume percent.

EXAMPLE 1

178 ml of 50% ethanol was added to 1000 ml of human blood plasma which was at a temperature of −2° C., the mixture was allowed to stand at −2° C. until a first precipitate was formed, and then was centrifuged to remove the first precipitate. To 900 ml of the resulting first supernatant liquid, which was adjusted to pH 6.0 with 0.8 M acetate buffer solution, was added 875 ml of 61% ethanol to bring the mixture to an ethanol concentration of 30%. The mixture was centrifuged to separate out a second precipitate (PI) consisting of gamma globulin and albumin from the second supernatant liquid. 71 g of this second precipitate was dissolved in a mixture of 5 ml of 4 M acetate buffer solution and 930 ml of distilled water. To the resulting solution was added 570 ml of 50% ethanol to provide an ethanol concentration of 16%, and the mixture was centrifuged. The resulting third supernatant liquid was adjusted to pH 5.0 with 1N NaOH, and to this supernatant liquid was added 431 ml of 50% ethanol to provide an ethanol concentration of 25%. The mixture was centrifuged resulting in a fourth precipitate, which was separated out and discarded, and a fourth supernatant liquid. The resulting fourth supernatant liquid was freeze-dried to obtain 5.5 g of a gamma globulin composition consisting of 90 wt. % of gamma globulin and 10 wt. % of albumin.

EXAMPLE 2

To 900 ml of the same first supernatant liquid as obtained in the first step of Example 1, which was adjusted to pH 6.5 with 0.8 M acetate buffer solution, 1200 ml of 61% ethanol was added to provide an ethanol concentration of 35%. The mixture was then centrifuged to separate out a second precipitate (PI). 80 g of the resulting second precipitate was dissolved in a mixture of 5 ml of 4 M acetate buffer solution and 1000 ml of distilled water. To the resulting solution 640 ml of 50% ethanol was added to provide an ethanol concentration of 16%, and the mixture was centrifuged. The resulting third supernatant liquid was adjusted to pH 5.0 with 1N NaOH, and to this third supernatant liquid was added 480 ml of 50% ethanol to provide an ethanol concentration of 25%. The mixture was centrifuged to separate a fourth precipitate, which was discarded, and a fourth supernatant liquid. The resulting fourth supernatant liquid was freeze-dried to obtain 6 g of a gamma globulin composition consisting of 92 wt. % of gamma globulin and 8 wt. % of albumin.

EXAMPLE 3

To 900 ml of the same supernatant liquid as obtained in the first step of Example 1, which was adjusted to pH 5.5 with 0.8 M acetate buffer solution, was added 875 ml of 61% ethanol to provide an ethanol concentration of 30%. The mixture was centrifuged to separate out a second precipitate (PI). 60 g of the resulting second precipitate was dissolved in a mixture of 5 ml of 4 M acetate buffer solution and 750 ml of distilled water. To the resulting solution was added 480 ml of 50% ethanol to provide an ethanol concentration of 16%, and the mixture was centrifuged to form a third precipitate, which was separated out and discarded, and a third supernatant liquid. The resulting third supernatant liquid was freeze-dried to obtain 4.9 g of a gamma globulin composition consisting of 95 wt. % of gamma globulin and 5 wt. % of albumin.

The gamma globulin compositions obtained in Examples 1 and 2 contained albumin in an amount of from 8 wt. % to 10 wt. % and had an anticomplementary activity value (ACA value) of less than 10 units/ml. Gamma globulin obtained in Example 3 contained albumin in an amount of 5 wt. % and had an ACA value of 12 units/ml. The gamma globulin compositions obtained in Examples 1, 2 and 3 are suitable for intravenous administration.

We claim:

1. A method of preparing a ganma globulin composition consisting of 90 to 95 wt. % gamma globulin and 5 to 10 wt. % albumin and which is suitable for intravenous administration, comprising the steps of:

mixing together a sample of human blood plasma and a quantity of ethanol to form a first mixture, said quantity of ethanol being sufficient to adjust the ethanol concentration of said first mixture to within the range of 8 to 9 vol. %, and holding said first mixture at a temperature of from 0° to −3° C. until a first precipitate and a first supernatant liquid are formed;

centrifuging said first mixture to separately obtain a first precipitate and said first supernatant liquid;

adding ethanol and a buffer to said first supernatant liquid to obtain a second mixture, the amount of ethanol added being such that the ethanol content of said second mixture is in the range of 30 to 35 vol. %, and the amount of said buffer added being such that the pH of said second mixture is adjusted by said buffer to a value within the range of 5.5 to 6.5, and the protein concentration of said second mixture is in the range of 1.0 to 2.0 wt. %, and then maintaining said second mixture at a temperature of approximately −5° C. until a second precipitate and a second supernatant liquid are formed;

centrifuging said second mixture to separately obtain said second precipitate and said second supernatant liquid;

suspending said second precipitate in water and adding a buffer thereto to form a third mixture, the amount of said buffer added being such that the pH of said third mixture is in the range of 4.0 to 5.0;

adding ethanol to said third mixture in an amount such that the ethanol concentration of said third mixture is in the range of 10 to 16 vol. %, and then maintaining said third mixture at a temperature of approximately −5° C. until a third precipitate and a third supernatant liquid are formed;

centrifuging said third mixture to separately obtain said third precipitate and said third supernatant liquid; and freeze-drying said third supernatant liquid to obtain said gamma globulin composition.

2. A method of preparing a gamma globulin composition consisting of 90 to 95 wt. % gamma globulin and 5 to 10 wt. % albumin and which is suitable for intravenous administration, comprising the steps of:

mixing together a sample of human blood plasma and a ethanol being sufficient to adjust the ethanol concentration of said first mixture to within the range of 8 to 9 vol. %, and holding said first mixture at a temperature of from 0° C. to −3° C. until a first precipitate and a first supernatant liquid are formed;

centrifuging said first mixture to separately obtain said first preciptitate and said first supernatant liquid;

adding ethanol and a buffer to said first supernatant liquid to obtain a second mixture, the amount of ethanol added being such that the ethanol content of said second mixture is in the range of 30 to 35 vol. %, and the amount of said buffer added being such that the pH of said second mixture is adjusted by said buffer to a value within the range of 5.5 to 6.5, and the protein concentration of said second mixture is in the range of 1.0 to 2.0 wt. %, and then maintaining said second mixture at a temperature of approximately −5° C. until a second precipitate and a second supernatant liquid are formed;

centrifuging said second mixture to separately obtain said second precipitate and said second supernatant liquid;

suspending said second precipitate in water and adding a buffer thereto to from a third mixture, the amount of said buffer added being such that the pH of said third mixture is in the range of 4.0 to 5.0;

adding ethanol to said third mixture in an amount such the range of 10 to 16 vol. %, and then maintaining said third mixture at a temperature of approximately −5° C. until a third precipitate and a third supernatant liquid are formed;

centrifuging said third mixture to separately obtain said third precipitate and said third supernatant liquid;

adding ethanol and a buffer to said third supernatant liquid to obtain a fourth mixture, the amount of ethanol being such that the ethanol content of said fourth mixture is in the range 20 to 25 vol. %, and the amount of said buffer added being such that the pH of said fourth mixture is adjusted by said buffer to a value within the range of 4.0 to 5.0, and then maintaining said fourth mixture at a temperature of approximately −5° C. until a fourth precipitate and a fourth supernatant liquid are formed, than centrifuging said fourth mixture to separately obtain said fourth precipitate and said fourth supernatant liquid, and then freeze-drying said fourth supernatant liquid to obtain said gamma globulin composition.

3. A method of preparing a gamma globulin composition consisting of 90 to 95 wt. % gamma globulin and 5 to 10 wt. % albumin, comprising the steps of:

mixing together a sample of human blood plasma and a quantity of ethanol to form a first mixture, said quantity of ethanol being sufficient to adjust the ethanol concentration of said first mixture to within the range of 8 to 9 vol. %, and holding said first mixture at a temperature of from 0° C. to −3° C. until a first precipitate and a first supernatant liquid are formed;

centrifuging said first mixture to separately obtain said first precipitate and said first supernatant liquid;

adding ethanol and a buffer to said first supernatant liquid to obtain a second mixture, the amount of ethanol added being such that the ethanol content of said second mixture is in the range of 30 to 35 vol. %, and the amount of said buffer added being such that the pH of said second mixture is adjusted by said buffer to a value within the range of 5.5 to 6.5, and the protein concentration of said second mixture is in the range of 1.9 to 2.0 wt. %, and then maintaining said second mixture at a temperature of approximately −5° C. until a second precipitate and a second supernatant liquid are formed;

centrifuging said second mixture to separately obtain said second precipitate and said second supernatant liquid;

suspending said second precipitate in water and adding a buffer thereto to form a third mixture, the amount of said buffer being such that the pH of said third mixture is in the range of 4.5 to 5.0;

adding ethanol to said third mixture in an amount such that the ethanol concentration of said third mixture is in the range of 20 to 25 vol. % and then maintaining said third mixture at a temperature of approximately −5° C. until a third precipitate and third supernatant liquid are formed;

centrifuging said third mixture to separately obtain said third precipitate and said third supernatant liquid; and adding ehanol, a buffer and NaCl to said third supernatant liquid to obtain a fourth mixture in amounts such that said fourth mixture has an ethanol content of 20 to 25 vol. %, a pH of 4.5 to 5.0 and an ionic strength of approximately 0.1, and then allowing said fourth mixture to stand until a fourth precipitate and a fourth supernatant liquid are formed;

centrifuging said fourth mixture to separate said fourth supernatant liquid from said fourth precipitate; and drying said fourth precipitate to obtain said gamma globulin composition.

* * * * *

UNITED STATES PATENT AND TRADEMARK OFFICE
CERTIFICATE OF CORRECTION

PATENT NO.   :   4 476 109
DATED        :   October 9, 1984
INVENTOR(S)  :   Tokusuke Kimura et al It is certified that error appears in the above-identified patent and that said Letters Patent is hereby corrected as shown below:

Column 4, line 22;   change "ganma" to ---gamma---.
Column 5, line  4;   after "a" insert ---quantity of ethanol to form a first mixture, said quantity of---.
Column 5, line 30;   change "from" to ---form---.
Column 5, line 35;   after "such" insert ---that the ethanol concentration of said third mixture is in---.
Column 5, line 45;   after "range" insert ---of---.
Column 5, line 52;   change "than" to ---then---.
Column 6, line 23;   change "1.9" to ---1.0---.
Column 6, line 43;   change "ehanol" to ---ethanol---.
Column 6, line 43;   change "NaCI" to ---NaCl---.

Signed and Sealed this

Twenty-third Day of July 1985

[SEAL]

Attest:

DONALD J. QUIGG

Attesting Officer    Acting Commissioner of Patents and Trademarks